(12) United States Patent
Scott

(10) Patent No.: US 6,266,995 B1
(45) Date of Patent: Jul. 31, 2001

(54) PORTABLE MEDICAL GAS SYSTEM TESTER

(75) Inventor: George L. Scott, So. Salem, NY (US)

(73) Assignee: Respiratory Management Services, Inc., Bedford Hills, NY (US)

(*) Notice: Subject to any disclaimer, the term of this patent is extended or adjusted under 35 U.S.C. 154(b) by 0 days.

(21) Appl. No.: 09/315,552

(22) Filed: May 20, 1999

(51) Int. Cl.[7] .......................... G01N 19/10; G01N 21/00; G01N 31/12; G01F 1/66
(52) U.S. Cl. ...................... 73/23.2; 73/31.01; 73/861.21; 422/83; 422/94
(58) Field of Search .................. 73/23.2, 23.31, 73/23.32, 23.34, 23.3, 31.01, 31.04, 861.21; 422/44, 83, 84, 94; 340/611, 573.1

(56) References Cited

U.S. PATENT DOCUMENTS

| | | |
|---|---|---|
| 4,267,721 | 5/1981 | Longenecker et al. . |
| 4,550,615 * | 11/1985 | Grant ................................ 73/861.21 |
| 4,848,163 | 7/1989 | Vacirca . |
| 5,057,822 * | 10/1991 | Hoffman .............................. 340/611 |
| 5,531,096 | 7/1996 | Castor . |
| 5,562,121 * | 10/1996 | Hodges et al. ........................ 137/360 |
| 5,569,922 | 10/1996 | Clarke . |
| 5,591,399 * | 1/1997 | GOldman et al. ..................... 422/44 |
| 5,741,959 | 4/1998 | Garcia, Jr. et al. . |
| 5,780,710 | 7/1998 | Murase et al. . |
| 5,780,716 | 7/1998 | Shimizu et al. . |
| 5,792,665 | 8/1998 | Morrow, III . |
| 5,920,263 * | 7/1999 | Huttenhoff et al. .............. 340/573.1 |
| 6,076,392 * | 6/2000 | Drzewiecki ........................... 73/23.2 |

OTHER PUBLICATIONS

Medical Gas Tester (undated) Modern Medical Systems Company, Farmingdale, NY 11735.

* cited by examiner

*Primary Examiner*—Daniel S. Larkin
*Assistant Examiner*—Jay I. Politzer
(74) *Attorney, Agent, or Firm*—Davidson, Davidson, & Kappel, LLC

(57) ABSTRACT

A portable medical gas system tester is small, lightweight, sturdy, self-contained and portable and can be either pen-activated and/or voice-activated so that it can be operated in the field by just one person. The device can test, collect and interpret data from all medical gas components, such as outlets, valves, alarms, central sources of supply and emergency low pressure oxygen fill connections, and with all medical gases including oxygen, air, vacuum, waste anesthetic gas disposal, nitrous oxide, nitrogen, carbon dioxide and carbon dioxide/oxygen mixtures. The device has a computer, a digital display device, an analog to digital converter, a gas sensor, a pressure and vacuum transducer coupled to the gas sensor, and an oxygen transducer coupled to the gas sensor, an exhaust outlet for venting excess gases to outside of the device's case, a bi-directional flow sensor coupled to gas sensor, and a flow transducer coupled to the flow sensor. The computer analyzes and interprets the electrical signals relative to predetermined values and generates a digital display for an operator to view.

38 Claims, 8 Drawing Sheets

PORTABLE MEDICAL GAS SYSTEM TESTER

BACKGROUND OF THE INVENTION

This invention relates to the field of medical gas system testers. More particularly, this invention relates to apparatus and equipment for testing characteristics of gas outlets, valves, alarms and sources of supply at medical facilities.

Medical gas systems deliver life-support gases throughout health care facilities (hospitals, skilled nursing facilities, clinics, dental offices, free-standing surgical centers, etc.) to outlets in patient care areas, for connection to medical devices such as ventilators and anesthesia machines. The gases are transported from central sources of supply, such as oxygen manifolds, through control equipment and piping systems, valves which are primarily for emergency shutoff, and local and master alarm systems. The typical piped medical gases are oxygen, medical air and vacuum, waste anesthetic gas disposal, nitrous oxide, nitrogen, carbon dioxide, carbon dioxide/oxygen mixtures, dental air and vacuum, and medical laboratory air and vacuum.

Testing and documentation of newly installed, renovated, repaired or breached medical gas systems, while obviously desirable, is presently required prior to use of those systems by patients. Two agencies that mandate the manner in which medical gas systems must be inspected are the Joint Commission on Accreditation of Healthcare Organizations (JCAHO), which is the primary accrediting agency for healthcare organizations in the United States, and the National Fire Protection Association (NFPA). The NFPA 99C Standard on Gas and Vacuum Systems, 1996 ed., has been adopted into law by most states and by numerous municipalities and mandates that certain characteristics of these systems be within a certain acceptable range, as certified by periodic inspection and testing. Testing of the medical gas delivery systems includes testing of the various gas lines to determine that the pressure, flow, oxygen concentration, vacuum and gas evacuation (suction) lines meet the proper medical flow or concentration levels and to ensure that these lines are not crossed.

Health care facilities generally manually collect the medical gas data that has been gathered in such tests. The methods currently used for collection of this data are cumbersome, inefficient and poorly suited to the emergent nature of the data required. For example, handwritten reports and reports generated by some devices currently in use do not collate and summarize the results, thereby requiring the tester to expend extra time to search through data for hundreds or thousands of medical gas components in order to find defects. Such extended delays in reporting to the facility may compromise patient safety, and the life-support nature of medical gas systems and components makes these delays undesirable and inappropriate.

In general, notebook-type portable computers require a convenient surface for the computer to rest during typing. Most patient areas, however, have limited space and accessibility at bedside, providing no room for the operator to rest the computer. Wheeled stands to support the computer are cumbersome and inefficient. At this time, a portable, wearable system for collecting data from all medical gas system components does not presently exist. There is a clear need for such a device that is simple, convenient to use and efficient.

At present, individual pressurized gas flow meters that are equipped with pressure gauges are generally custom-assembled in order to functionally test medical gas outlets. One commercially available unit, distributed by the Squire-Cogswell Company under the name 5310 Vac-U-Test, is limited to testing air and vacuum outlets. This device is inefficient and cumbersome to use because separate vacuum flow meters with vacuum gauges must be used for vacuum inlets. Moreover, an oxygen analyzer is also needed, either separately or incorporated into the flow meter/gauge assembly. This device is further inefficient because documentation is carried out with a pencil, paper forms and a clipboard, which means that the operator must release two flow testers from his grip in order to record the data. In addition, the operator must remember numerous subjective problems and NFPA 99 specifications for flow, pressure, alarm low and high activation points, etc. for each of the various gases. In other words, these test points and specifications are not automatically tested and verified.

In many instances the collected data for outlets, alarms, valves and gas analysis is incorporated into a typed report for the client. Unfortunately, the hand tabulation that must first be done is time-consuming and results in delays in submitting the report. Therefore, in most instances, the health care facility receives only limited rough data with a cover page. Presently, most testing companies and hospitals provide few exception findings and do not recommend corrective action. At least one testing company is known to have the data manually typed into a notebook computer for later presentation to the client. Unfortunately, the spreadsheet format in which the data is presented restricts the amount and types of data that can be collected, and, again, exception findings are very limited, with no recommendations being given for corrective action. Therefore, because the data collection device is not a database, its value is limited to manual data collection and presentation.

One other commercially available medical gas tester is a portable, wearable device sold by National Safety Technologies, Inc. (NST) under the name G2500 Medical Gas Outlet Analyzer. This device is not used by many in the industry, presumably because the inputting of identifier data is done slowly and inefficiently, as each individual letter of the alphabet must be found by use of directional arrows and then displayed. Also, the choice of subjective findings is limited, and the device does not accurately analyze or record oxygen concentration for pressurized outlets, as required by NFPA 99 and others. In addition, this device can test only outlets, but not all other required components of a medical gas system, such as valves, alarms and central sources of supply, as required by NFPA 99 and others.

Also, the reports generated by this device do not collate or summarize the results. This means that valuable extra time is required in order for the person reviewing the reports to search through data for many medical gas components in order to locate defects. Furthermore, the NST device is not sufficient because storage of input is limited to 1,500 outlets at a time. Thus, because data must be downloaded to a host computer periodically, it is impractical for use by larger hospitals that have 5,000 or more outlets. Finally, in order to generate a report or to view more than several outlets at once, the information and data gathered by the NST device must be downloaded to a personal computer running special NST software.

Accordingly, it is desirable to provide a medical gas system tester that solves all these inefficiencies and deficiencies. It is desirable to provide a medical gas system testing computer that is hand-held and portable and that can test, collect, enter and interpret data from all medical gas sources and components.

SUMMARY OF THE INVENTION

Accordingly, it is one object of the present invention to provide a medical gas system tester that is portable and hand-held.

It is another object of the present invention to provide a medical gas system tester that can efficiently test, collect and interpret all data from medical gas components at a medical facility.

It is a further object of the present invention to provide a medical gas system tester that can collate, summarize and analyze test data collected and prepare reports based thereon.

It is yet another object of the present invention to provide a medical system tester that, due to its portability and ease of use, allows an operator with limited computer and keyboard skills to quickly, efficiently and cost effectively test all medical gas components in health care facilities.

It is still another object of the present invention to provide a medical gas system tester that can record all data presently required for compliance with the NFPA 99 Standard for certifications, periodic inspections, repairs of defective components and consultations.

It is yet a further object of the present invention to provide a medical gas system tester that can be used in patient care areas and also in mechanical rooms, manifold rooms, as well as outside at bulk oxygen sites where wheeled stands are impractical.

In accordance with these and other objects of the invention, the portable medical gas system tester of the present invention is small in size, light in weight, sturdy in construction, self-contained and portable so that it can be transported and operated in various medical and other facilities. In addition, the portable medical gas tester is designed to be user friendly and battery-powered and can be either pen-activated and/or voice-activated so that it can be operated in the field, i.e., at medical facilities, by just one person. This portable gas system tester has the ability to test, collect and interpret data from all medical gas components, such as outlets, valves, alarms, central sources of supply and emergency low pressure oxygen fill connections. Sources of supply include medical air compressors, vacuum pumps, waste anesthetic gas disposal pumps, gas manifolds and bulk liquefied gas supplies. The tester is designed to function with all dental, medical laboratory and health care facility medical gases including oxygen, air, vacuum, waste anesthetic gas disposal, nitrous oxide, nitrogen, carbon dioxide and carbon dioxide/oxygen mixtures. Flow for gases of differing densities, such as nitrous oxide and carbon dioxide, is compensated for by the software program. The cross connection tests and outlet/inlet repair documentation required by the National Fire Protection Association (NFPA) 99 Standard for Health Care Facilities are also performed. The software further allows for documentation of field and laboratory data.

In a preferred embodiment, the medical gas system testing apparatus of the present invention has the capability of multiple function testing and analysis of medical gas dispensing systems. Such an apparatus comprises a computer, a digital display device such as a screen, an analog to digital converter whose output is connected to the digital display, a gas sensor for sensing gas data from medical gas dispensing systems, a pressure and vacuum transducer coupled to the gas sensor for producing an electrical signal related to the gas pressure or vacuum sensed by the sensing device and transmitting the signal to the computer, and an oxygen transducer coupled to the gas sensor for producing an electrical signal related to the concentration of oxygen sensed by the gas sensor and transmitting the signal to the computer. The apparatus also has an exhaust outlet for venting excess oxidizing and other gases to outside of the device's case, a bidirectional flow sensor coupled to gas sensor for sensing the rate of gas flow from medical gas dispensing systems, and a flow transducer coupled to the flow sensor for producing an electrical signal related to the gas flow rate and transmitting the signal to the computer. The computer analyzes and interprets the electrical signals relative to predetermined values and generates a digital display for an operator to view.

BRIEF DESCRIPTION OF THE DRAWINGS

The above and other objects and advantages of the invention will be apparent upon consideration of the following detailed description, taken in conjunction with the accompanying drawings, in which the reference characters refer to like parts throughout and in which.

DETAILED DESCRIPTION OF THE INVENTION

Figure 1:
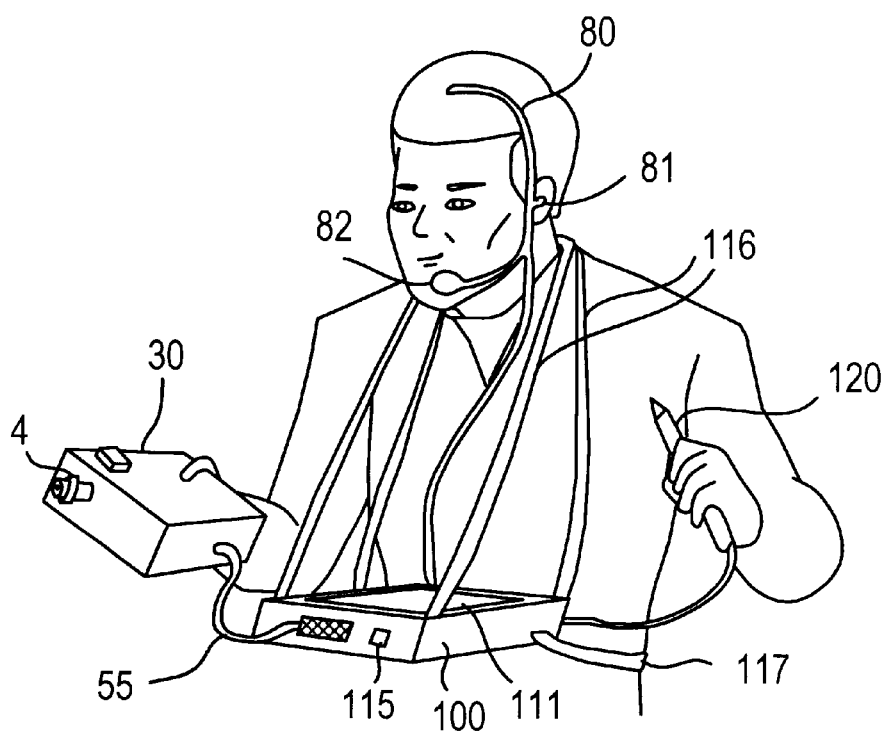
FIG. 1 shows graphical representation of an operator using one embodiment of the medical gas system testing apparatus of the present invention.
Figure 2:
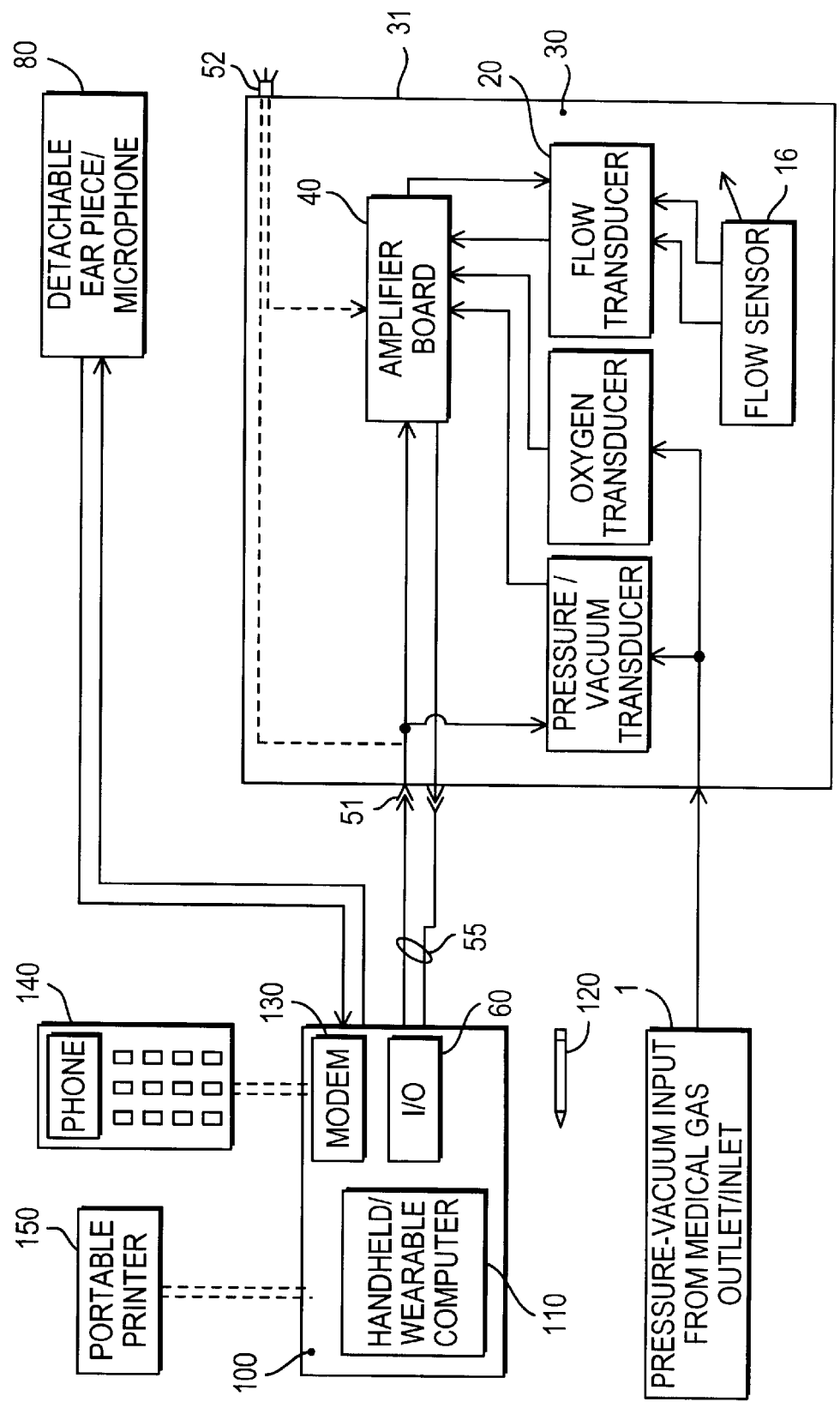
FIG. 2 shows an electrical block diagram of the components of the medical gas tester of the invention.

Referring now to the drawings, in particular to FIGS. 1 and 2, the portable medical gas system tester of the present invention has several primary components. The apparatus has a housing 100, within which is a computer or microprocessor 110. Computer 110 can be one of many that are well-known in the art that are suitable for the particlur functions discussed herein. In the preferred embodiment, computer 110 is a commercially-available Pentium®-based, 1.6 GB internal hard drive tablet computer with a Windows® operating system. Computer 110 is also equipped with a hard drive memory for long term data storage a random access memory (RAM) for short term data storage. Computer 110 can store all the collected data from numerous large medical centers due to the large storage capacity of its hard drive.

Computer 110 is coupled to a proprietary outlet analyzer 30 for analysis of all data that is collected by outlet analyzer 30. Data is transferred from outlet analyzer 30 to computer 110 by any of the known means in the art. In the preferred embodiment, this link is made via a flexible umbilical electrical cable 55. Field gas analysis instruments that export data via an RS232 connector can be connected to computer 100 via cable to the computer's RS232 connection (not shown).

Computer 110 is preferably adapted to process custom application, data collection and report generation software, as will be discussed more fully below. For convenience of the operator and ease of input, the preferred embodiment of the device also utilizes several effort-saving devices, such as a pen 120 for input of data onto a screen 111. Pen 120 allows the operator to enter data without having to manually type data, by any of the well known pen/screen input methods such as light, pressure, flux and others. A PCMCIA data acquisition analog-to-digital converter and input/output card 60 cooperate to accept input for computer 110. In addition, a PCMCIA fax/modem card 130 can be inserted for remote data transmission and acquisition.

Computer 110 can also utilize a detachable headset 80, which includes an earpiece speaker 81 and miniature microphone 82 and is connected to the audio jacks of computer 110 for voice command input during outlet testing and for other functions as needed. Use of voice commands in cooperation with voice recognition software allows computer 110 to be operated in a "hands-free" mode, thereby freeing the operator's hands for inserting outlet analyzer 30 into outlets and inlets as needed. The use of headset 80 also allows for automated documentation of test results, which greatly increases productivity, thereby decreasing costs to health care facilities.

Two additional peripherals can be used with computer 110 in order to increase its functionality are a cellular or land-line telephone 140 and a portable printer 150. Cellular or land-line telephone 140 can be connected to fax/modem card 130 with a phone line as needed such that data files or entire reports can be transmitted to a remote personal computer or network for storage or printing. Similarly, the data or reports can be transmitted via telephone 140 from computer 110 for printout on a remote fax machine. Thus, at the end of a session, project, work day or other period, information can be downloaded to a host computer for integration of test reports from multiple devices.

Portable printer 150 is used to print on-site reports. Printer 150 is connected to computer 110 via a wireless infrared port or via a standard printer cable to the computer's serial or parallel port. Printer 150 enables medical gas computer 110 to act as a stand alone system.

Computer 110 can also exchange collected data from other medical gas testing computers by way of an infrared transfer port 115. This is accomplished by placing two computers within one meter of each other's infrared transfer ports 115 such that data can be exchanged via infrared transfer. This enables a single medical gas testing computer 100 to generate an integrated and collated on-site report when multiple (unlimited) computers are used in the same facility. In addition, computer 110 can download data and files to a host personal computer for report generation and for integration with data that was collected previously for a specific healthcare facility.

The medical gas system testing device 100 of the current invention can be used as a hands-free wearable device during outlet and inlet testing, as illustrated in FIG. 1, by means of a custom neck strap 116 and belt attachments 117. Testing of other medical gas components can be performed in either the hand-held or the wearable configuration. In a preferred embodiment, the component-filled housing 100 is small and lightweight. In one most preferred embodiment, the device 100 could weigh less than four pounds and be approximately 11"×7½"×2" in size. Outlet analyzer 30, which contains the pneumatic flow train and electronic circuitry as discussed below, should be similarly small in size, being less than 3½"×7"×2" in size and weighing less than approximately 36 ounces in one most preferred embodiment. The small and compact size of both the main housing 100 and outlet analyzer 30 allows this device to be easily carried from site to site and most conveniently worn about the operator's neck or at the operator's belt region.

Outlet analyzer 30 receives electrical power, preferably 5 Volts DC, from computer housing 100 via PCMCIA data acquisition, analog-to-digital converter and input/output card 60 by way of cable 55. The amplifier circuit board 40, which preferably includes a 12 Volt DC power regulation circuit, provides 12 Volts DC to amplifier circuit board 40 itself and to flow transducer 20. Alternatively, a power regulation circuit can be separate and apart from amplifier circuit board 40 and provide 12 Volts DC to amplifier circuit board 40 and to flow transducer 20.

Figure 3:
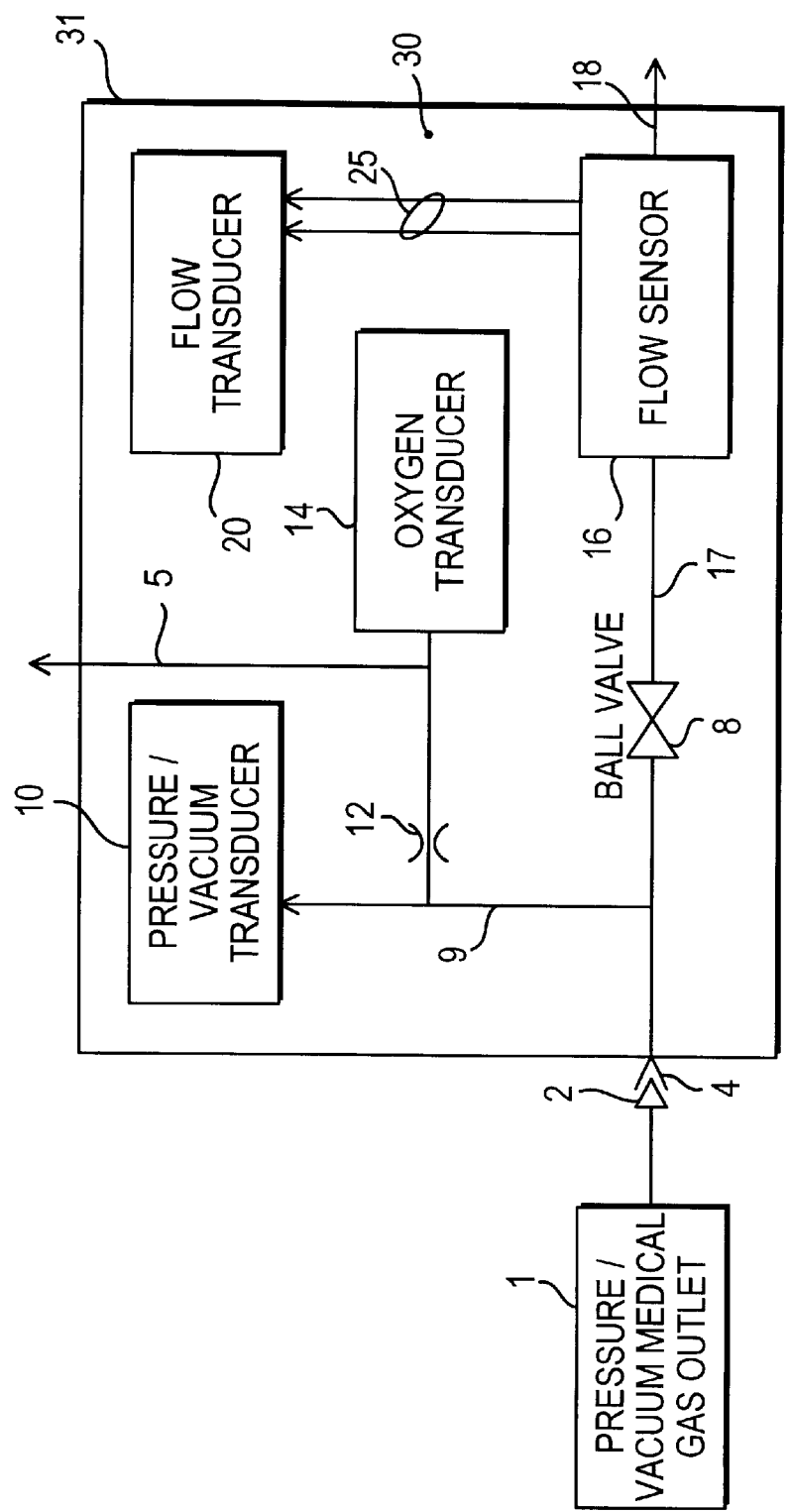
FIG. 3 shows a pneumatic block diagram of the components of this invention.

As shown more particularly in FIG. 3, outlet analyzer 30 has a case or housing 31 to the exterior of which a medical gas specific interchangeable wall adapter 2,4 is attached. Quick connect adapters 2 are interchangeable adapters that can be attached to the in/out gas port 4 of outlet analyzer 30 in order to allow analyzer 30 to connect to different gas ports. Typically, the wall adapters have a male quick connect adapter 2 which mates with a female quick connect inlet adapter 4 on analyzer 30 so that mating is simple. It should be noted that, typically, each of the various medical gas outlets, such as oxygen, air, vacuum, etc., has a different port so that the same inlet port cannot be connected to each, and an adapter is required. Once the adapter is connected, the operator signals to computer 110 that, for example, oxygen is being sensed, and certain channels will be activated. One such type of quick-connect outlet is a Chemetron-type medical gas wall/ceiling outlets, which is gas specific for the services indicated and accepts only corresponding Chemetron-type quick-connect adapters.

Outlet analyzer 30 also has a manually controlled ball valve 8 pneumatically coupled to the outlet adapter 4, a bidirectional flow sensor 16, two flow transducer tubes 25, a connecting adapter 17, and an exhaust outlet 18. A bi-directional flow sensor 16 is necessary, although separate uni-directional flow sensors can be used, in order to measure both pressure (positive gas flow) and vacuum (negative gas flow) accurately. High pressure connectors and tubing 9 connect a restrictor 12 to an oxygen transducer 14, and, via exhaust tubing 5, to outside the outlet analyzer case 31. As shown in FIGS. 2 and 3, Outlet analyzer 30 further consists of a pressure/vacuum transducer 10, a differential flow transducer 20, a proprietary power regulation, amplifier and signal conditioning circuit board 40, an umbilical cable connector 51 and an optional light emitting diode (LED) 52.

In this invention, the medical gas system testing device can perform the functions of inspection, testing and data collection of medical gas inlet and outlets, valves, alarms, central sources of supply with associated central devices, emergency low pressure oxygen fill systems, and gas analysis. All of these functions are accomplished using proprietary software. In the preferred embodiment, the software program is designed to provide specific on-screen 111 prompts to the operator during each function and to interpret responses based upon the type of testing being performed, such as certification, periodic inspection, repair or consultation. The software program further distinguishes the NFPA 99 edition year specifications to which the certification is being performed such that the parameters are automatically changed depending on the edition year used. In one embodiment, for example, the edition year is entered by the operator prior to the certification/inspection, and the software program automatically flags out-of-specification inputs, provides line item detail, a summary of findings and cost-effective recommendations for each medical gas component.

In addition, in a preferred embodiment, the software program interprets the collected data and compares it to the requirements of different editions of the NFPA 99 medical gas system certifications and periodic inspections standard. The software program automatically flags out-of-specification data inputs with an appropriate warning, provides line item detail, a summary of findings and cost effective recommendations for each finding.

In a most preferred embodiment of the invention, data input collection is accomplished primarily through pre-defined, easy-to-use menus and multiple choice selections that are selected by the operator by pointing to the appropriate choice on computer screen 111 with pen 120. The few choices that require non-programmed responses are entered into a custom-designed pull-down on-screen 111 keyboard, onto which information is "typed" using pen 120. Alternately, the operator may "write" letters onto screen 111 in print using pen 120. The handwriting recognition program converts the "handwritten" printed letters into words that are "understood" and processed.

The proprietary software should be specifically designed for fast data collection and for use by an operator with limited computer and keyboarding experience. Audio/visual alerts are built into the software to alert the operator to take additional action in selected, dangerous situations, such as an instruction for the operator to "Place DO NOT USE TAG" on a defective or inoperative warning alarm. Audio/visual alerts are also activated where common errors are known to occur in the inspection process.

As discussed above, the medical gas testing computer device can also be used as a stand alone system when connected to a portable printer 150 for on-site generated reports. Also, data can be downloaded to a host computer for integration with the facilities' previously collected data and for generation of reports. Information can also be transmitted into computer 110 by fax or modem 130 via the internal PCMCIA card 60 when connected to a cellular, portable or land line phone 140.

The device operates to measure gas data as follows. As shown in FIGS. 2 and 3, a medical gas specific interchangeable wall adapter 2 with a male or female quick-connect adapter is inserted into the mating quick-connect inlet adapter 4 of outlet analyzer 30. The proper adapter must be used for vacuum or flow and for the specific gas measured. The operator then attaches interchangeable wall adapter 2 to a medical gas outlet 1 or vacuum inlet 1, which transmits pressure or vacuum via high pressure connectors and tubing 9 to the static pressure/vacuum transducer 10. Transducer 10 produces an electrical signal proportional to the static pressure (from 0 to 200 psig) and static vacuum (0 to –29 inches of mercury) applied to it. This electrical signal is transmitted to the outlet analyzer amplifier and signal conditioning circuit board 40, then, via the flexible umbilical electrical cable 55 to the PCMCIA data acquisition, analog to digital converter and input/output card 60, inserted into the computer 110, for processing by the system's proprietary software program.

Pressure is also transmitted to a calibrated flow restrictor 12 which significantly decreases the flow and pressure to the oxygen transducer 14. Excess gas is transferred to the atmosphere outside the outlet analyzer case 31 via exhaust tubing 5 in order to decrease the likelihood of oxidizing gases accumulating within outlet analyzer case 31. Ball valve 8, which is normally closed, prevents pressure or vacuum from passing beyond this point.

Flow is captured differently by computer 110 and the sensor head for pressurized gases and for vacuum, based upon the applicable pressure and vacuum standard of NFPA 99. The choice of which formulae and processes are to be used by outlet analyzer 30 and computer 110 are determined by the type of voice gas command previously stated by the operator and confirmed by the output of transducers 10,20.

For pressurized gases, positive gas flow is measured as follows, as mandated by NFPA 99. Once interchangeable wall adapter 2 to a medical gas outlet 1 are connected, static pressure/vacuum transducer 10 instantaneously measures the static gas pressure. The operator then, manually and slowly, partially opens ball valve 8 to cause gas to flow through bi-directional flow sensor 16. When the pressure drops 5 psig from the initial static pressure reading, as sensed in real time by static pressure/vacuum transducer 10 and associated hardware 40, 55, 60, 100 and proprietary software; the flow rate—30 to 300 liters per minute (LPM)—is measured in real time by means of the differential pressure generated across flow sensor 16. The pressure is transmitted from flow sensor 16 to flow transducer 20 via two tubes 25, where flow transducer 20 produces an electrical signal proportional to the differential pressure.

The electrical signal produced by flow transducer 20 is transmitted to outlet analyzer amplifier and signal conditioning circuit board 40 then, via flexible electrical cable 55, to PCMCIA data acquisition analog-to-digital converter and input/output card 60 that has been inserted into computer 100 for processing by the system's proprietary software program. At the 5 psig drop, the millivolt output of flow transducer 20 is read and the flow rate is computed, based on the specific pre-input characteristics of the gas whose flow is being measured. Since the specific gravity and density differs for each gas, the system software contains an adjustment coefficient for each gas to translate flow sensor measurements into the flow rate measurement for the gas analyzed. The system thus compensates for the different gas densities and converts the flow sensor measurement into a correct flow rate for that gas.

In addition, a software-controlled, computer-generated audio signal is received by the operator in his headset 80 ear piece 81 when the pressure drops 5 psig from the initial static pressure, and the operator is signaled to close ball valve 8, as the desired pressure drop has been achieved. Alternatively, light emitting diode (LED) 52 incorporated into the outlet analyzer 30 could be lit as a signal to the operator that the pressure has dropped 5 psig. Upon hearing the sound cue via audio signal or seeing the optional visual cue via lit LED, the operator closes ball valve 8, thereby stopping the flow of gas through flow sensor 16.

Simultaneously with the processing of pressure and flow signals, oxygen transducer 14 sends an electrical signal proportional to the oxygen concentration (0 to 100%) through amplifier and signal conditioning circuit board 40. This signal is then transmitted via flexible electrical cable 55 to PCMCIA data acquisition analog digital converter and output card 60 for real-time processing by computer 100 using the proprietary software. The system analyzes and documents outlet oxygen concentration from 0 to 100% with an accuracy of approximately 2%.

For measurement of vacuum and waste anesthetic gas disposal (WAGD), negative flow (vacuum) is measured as follows. First, a specific wall adapter 2 is attached to adapter 4 of outlet analyzer 30, and interchangeable wall adapter 2 is connected to a vacuum inlet 1, whereupon static pressure/vacuum transducer 10 instantaneously measures the static pressure. Then, the operator manually opens ball valve 8 fully. In vacuum and waste anesthetic gas disposal (WAGD), the flow is in the opposite direction to the flow of pressurized gases, and the flow is measured in real time by bi-directional flow sensor 16, flow transducer 20 and associated hardware 40, 55, 60, 100, in a process similar to that discussed above regarding pressurized gases, but incorporating different proprietary software.

Figure 4A:
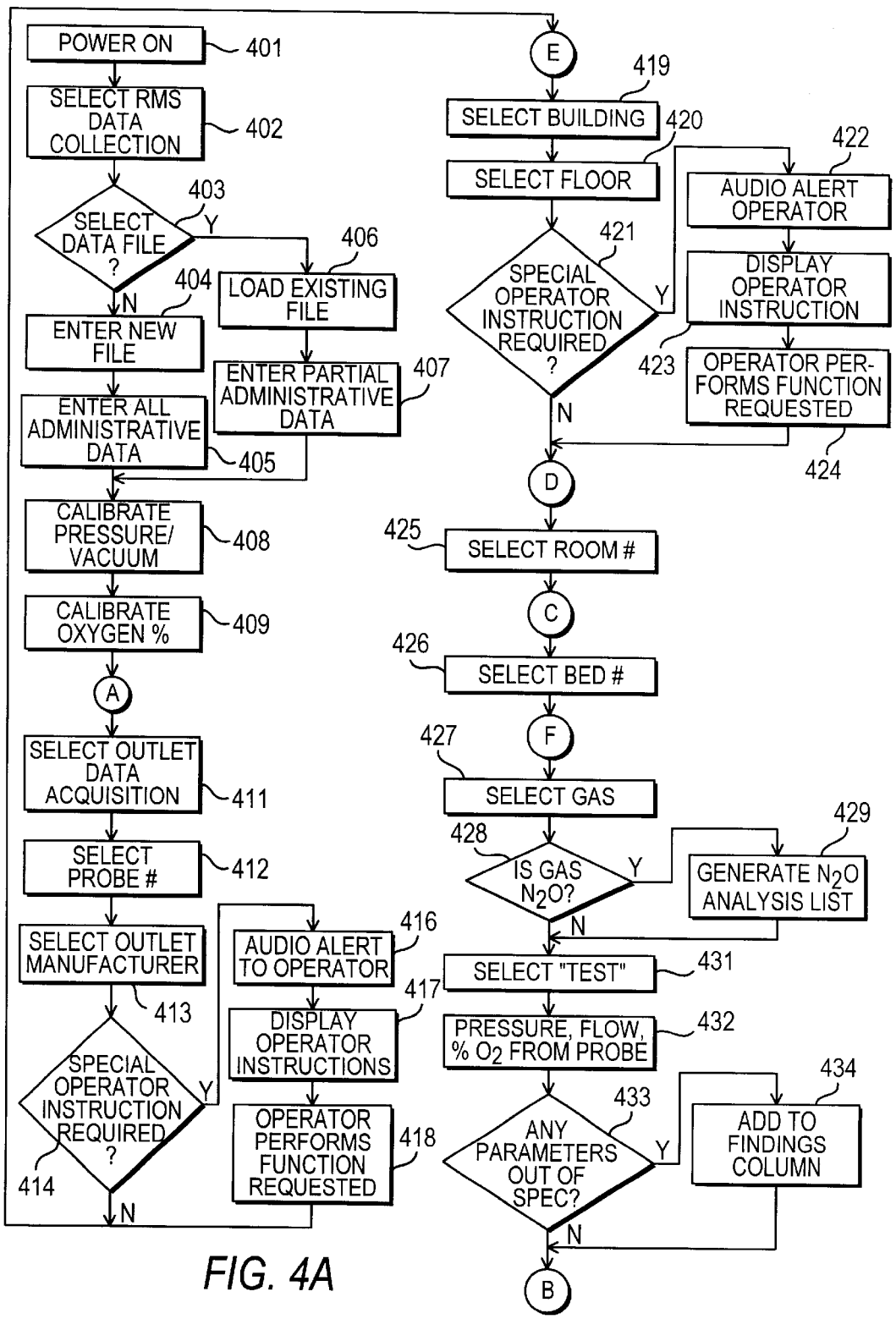
FIGS. 4A and 4B shows a flow chart of the steps of outlet data acquisition.

The medical gas testing computer device must measure flow rate, either positive or negative, as well as gas concentrations at the various outlets, and must also test the master and area alarms for information about a specific gas system, as to whether it is not functional or not according to specification. In general, the operator can input data into computer 100 either via voice, through the wearable microphone 80, internal sound card and appropriate voice- and sound-recognition software, or via pen 120 input directly to computer screen 111. As shown in FIG. 4A, once power has been turned on 401, the data collection system is activated, such as outlets, valves or alarms, is entered 402 so that the proper programs can be accessed. The data file is selected 404,406 and appropriate administrative data is entered 405, 407. The operator then calibrates pressure and vacuum 408 and the oxygen concentration 409 which function is performed automatically by the custom software. Then the operator chooses whether the data collection is for an outlet 411, as shown in FIGS. 4A and 4B, or for a valve 501, as shown in FIG. 5, or alarms 601, as shown in FIG. 6A.

Figure 4B:
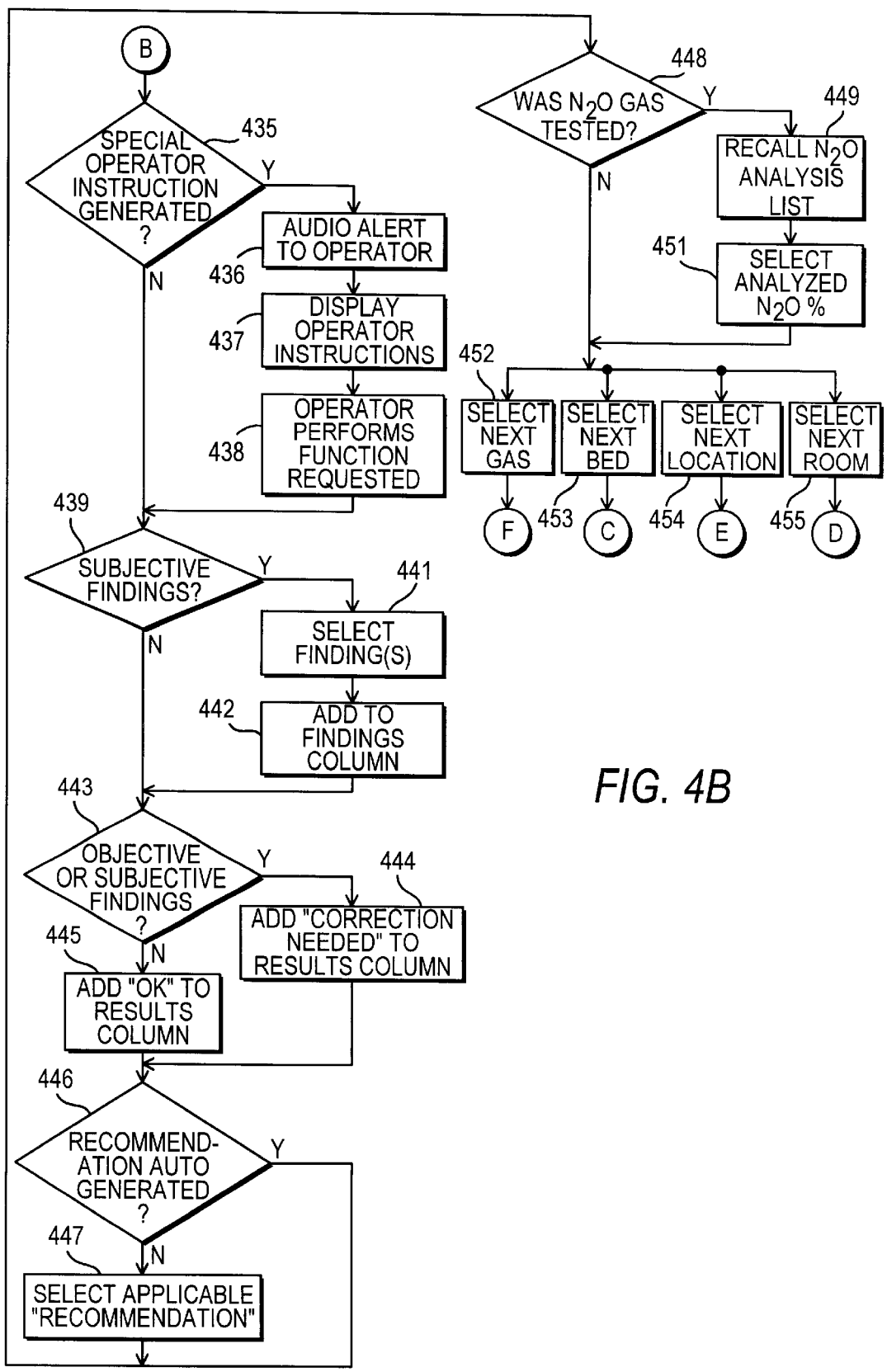

For outlet data acquisition, the medical gas testing device of this invention operates according to the steps shown in FIGS. 4A and 4B. Prior to actually testing medical gas outlets or inlets, the operator inputs location identifiers into computer 110, such as Operator instructions 414–418, Facility, Building 419, Floor 420, Outlet Manufacturer, Room 425 and Bed 426. Once the location of an outlet to be tested has been described, the operator inputs the gas type 427, such as "oxygen". This information is input preferably, as described earlier, by the operator speaking the word "oxygen" into microphone 82 but may also be input manually or using pen 120. This command prompts computer 110 and outlet analyzer to stand by to receive and process data from the outlets or inlets 1 specific to the gas type identified by the operator. The gas test is chosen 431, and pressure, flow or gas concentration is measured by outlet analyzer 30.

The unit is pre-programmed with gas-specific, predefined limits for quantifiable data, such as static pressure, vacuum, flow and oxygen concentration, such that the device automatically determines whether the gas flow from a particular outlet or inlet is acceptable or unacceptable. The results of the test(s) are displayed on wearable computer screen 111. Data that does not fall within the prescribed limits are automatically flagged and entered into the findings column on computer screen 111 and into any the onsite reports or final facility reports that are generated. Analyzer 30 the determines based upon these prescribed values whether or not any of the measurements are "out of spec", i.e., whether they fall outside the acceptable parameters for that particular gas, and these findings are added to a findings column 434. The operator can also add any observed objective or subjective findings to the findings column 439–444, and can generate a specific recommendation 447 based upon a preset list of recommendations. The custom software program will also automatically generate recommendations 446 based upon the specific findings reported. For nitrous oxide, specific analyses are performed 428–428, 449–451, according to preset conditions. The operator can continue by inputting a new location identifier and repeating this procedure.

Figure 5:
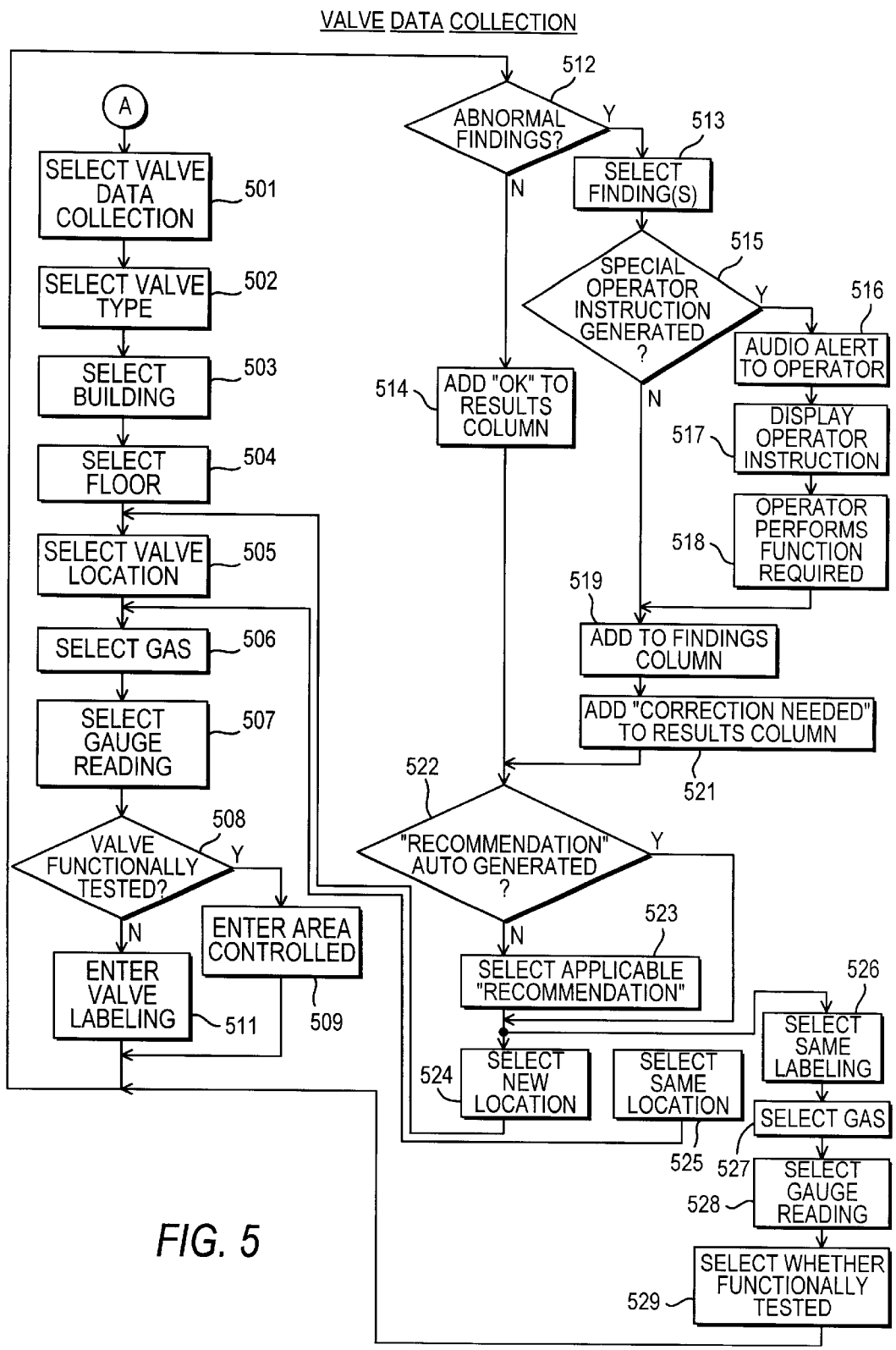
FIG. 5 shows a flow chart of the steps of valve data collection.
Figure 6A:
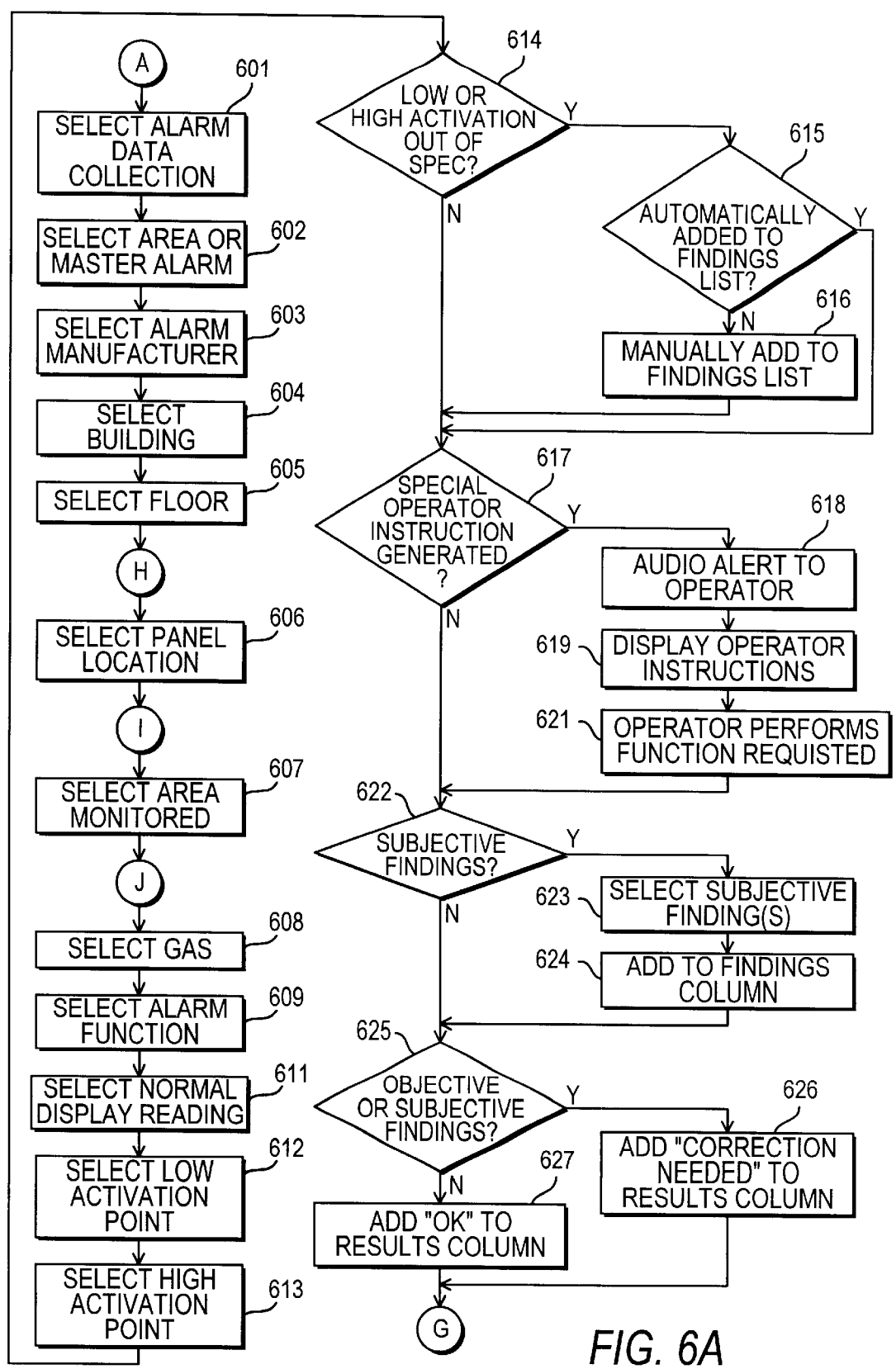
FIGS. 6A and 6B show a flow chart of the steps of master and area alarm data collection.

A similar process illustrated in FIG. 5 is done for data acquisition and testing of valves, which isolate and control the individual outlets. The valve location identifiers are input 502–505, and the specific valve gas is identified 506. The valve gauge reading is taken 507, and the valve is either functionally tested 508 or the valve labeling is examined 511. If any abnormal findings are detected 512, appropriate findings are entered 519 and flagged 521 that a correction is needed. A recommendation can automatically be generated 522 or one of the pre-input recommendations 523 selected. The operator can continue by inputting new location or gas identifiers 524–527 and repeating this procedure.

Figure 6B:
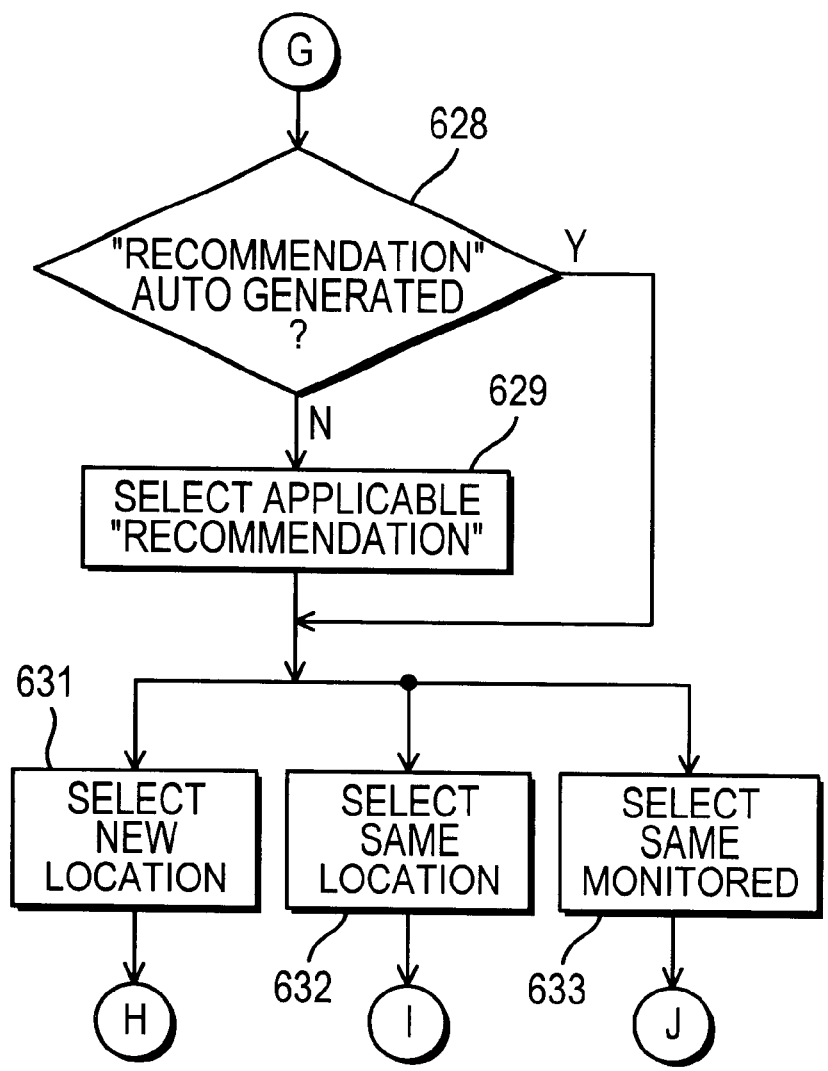

A similar process illustrated in FIGS. 6A and 6B is done for data acquisition and testing of master and area alarms, which provide notice if a specific gas system pressure or function is out of specification. Once the alarm data collection setting is chosen 601, alarm identifiers 602,603 and location identifiers 604–607 are input, and the specific alarm gas is identified 608. A normal reading parameter is input 611, and low and high activation points are also input 612,613 in order to determine the parameters of specification. If the alarm is found to be out of spec 614, certain findings can be added to the findings list either automatically 615 or manually 616 or with subjective 622–624 findings and flagged 625,626. Based upon these findings, recommendations can be automatically 628 or manually 629 be generated based upon pre-input findings and recommendations correlations. The operator can continue by inputting new location or area identifiers 631–633 and repeating this procedure.

In addition, through use of the voice-recognition software or pen input, the operator can enter any of numerous predefined subjective, programmed findings to said outlet data by speaking one or two preset words or a preset phrase into the wearable microphone 80 incorporated into the headset. After interpreting the words system by the operator, the proprietary software program will enter the corresponding phrase or sentence on computer screen 110 and into the on-site report and final report. For example, the operator may say "Retain" into microphone 80 and the software will print a phrase such as, "Outlet will not retain or release medical devices" onto screen 110. All dictated and outlet analyzer 30 "captured" entries can be quality-assured by the operator by viewing computer screen 110, and changed, if needed, by simple pen 120 strokes on computer screen 110. The operator can view more than twenty prior outlet test results at a time. Backward scrolling makes all previous testing accessible. Thus, with a single pen stroke or voice command, the invention documents over one hundred subjective problems and exceptions to medical gas standards and lists recommendation to correct each.

When not functionally testing outlets, outlet analyzer 30 may be stored by attaching it to a proprietary design belt 117 worn by the operator allowing his hands to be free for other functions. Umbilical cable 55 may also be disconnected from computer 110, thereby allowing outlet analyzer 30 and cable 55 to be stored for later use.

Thus, a new and improved medical gas tester is provided. One skilled in the art will appreciate that the present invention can be practiced by other than the described embodiments, which are provided for purposes of illustration and not limitation, and the present invention is limited only by the claims that follow.

What is claimed is:

1. An apparatus for multiple function testing and analysis of a medical gas dispensing systems, comprising:
   a computing device;
   an electronically operated digital display device coupled to said computing device;
   a sensing device for sensing data from medical gas dispensing systems;
   a pressure and vacuum transducer coupled to said sensing device for producing an electrical signal related to the gas pressure or vacuum sensed by said sensing device, said signal being transmitted to said computing device;

an oxygen transducer coupled to said sensing device for producing an electrical signal related to the concentration of oxygen sensed by said sensing device, said signal being transmitted to said computing device;

an exhaust outlet for venting excess oxidizing and other gases to outside of said sensing device;

a bi-directional flow sensor coupled to said sensing device for sensing the rate of gas flow from medical gas dispensing systems; and a flow transducer coupled to said flow sensor for producing an electrical signal related to the gas flow rate, said signal being transmitted to said computing device;

wherein said computing device analyzes and interprets said electrical signals relative to predetermined values and generates a display on said digital display device for an operator of said device to view.

2. The apparatus of claim 1 further comprising a structural casing, wherein said structural casing houses said analog-to-digital converter, said pressure and vacuum transducer, said oxygen transducer, said bi-directional flow sensor and said flow transducer.

3. The apparatus of claim 2, wherein said sensing device is situated external to said structural housing.

4. The apparatus of claim 3, wherein said sensing device comprises an interchangeable wall adapter for connection to a medical gas supply.

5. The apparatus of claim 2, wherein said structural housing is lightweight and is easily portable by said operator of said device.

6. The apparatus of claim 1 further comprising a manually-controlled ball valve for controlling gas flow through said bidirectional flow sensor.

7. The apparatus of claim 6, wherein said ball valve is situated upstream of said bidirectional flow sensor, wherein said ball valve is opened partially to allow gas to flow through said flow sensor such that gas flow rate is measured by differential pressure generated across said flow sensor.

8. The apparatus of claim 7 further comprising operator signaling means for signaling said operator of said device that pressure sensed by said sensing device has changed by a predetermined amount and that said ball valve should be closed.

9. The apparatus of claim 8 further comprising an earphone, wherein said signaling means comprises an audio signal generated by said computing means that is audible by said operator through said earphone for signaling to said operator.

10. The apparatus of claim 8, wherein said signaling means comprises visual signals generated by said computing means that are visible to said operator of said device for signaling to said operator.

11. The apparatus of claim 10, wherein said visual signals are displayed on said display device and are visible by said operator.

12. The apparatus of claim 1 further comprising operator signaling means for signaling to said operator of said device.

13. The apparatus of claim 12 further comprising an earphone, wherein said operator signaling means comprises audio signals generated by said computing device that are audible by said operator of said device through said earphone for signaling to said operator.

14. The apparatus of claim 12, wherein said signaling means comprises visual signals generated by said computing means that are visible to said operator of said device for signaling to said operator.

15. The apparatus of claim 14, wherein said visual signals are displayed on said display device and are visible by said operator.

16. The apparatus of claim 1 further comprising data input means.

17. The apparatus of claim 16, wherein said data input means comprises a keyboard.

18. The apparatus of claim 16, wherein said data input means comprises touch-sensitive display means.

19. The apparatus of claim 16, wherein said data input means comprises a photosensitive display screen and a light pen.

20. The apparatus of claim 16, wherein said data input comprises a microphone, wherein said computing device senses audio signals spoken by said operator of said device for signaling to said device.

21. An apparatus for testing and analysis of a medical gas system, comprising:

a computing device;

a display device coupled to said computing device;

a hand-held sensor for sensing data from said medical gas system, said sensor including a housing and at least one connector for mating with an outlet or inlet of said medical gas system;

a pressure or vacuum transducer within said housing for producing an electrical signal related to the gas pressure or vacuum sensed by said sensor, said electrical gas pressure or vacuum signal being transmitted to said computing device; and a flow sensing device within said housing for producing an electrical signal related to the gas flow rate sensed by said sensor, said electrical gas flow rate signal being transmitted to said computing device;

wherein said computing device interprets said electrical signals and generates a display on said display device related to the status or operation of said medical gas system.

22. The apparatus of claim 21 further comprising interchangeable adapters that attach to said connector and are specific to mate with the outlet or inlet for a specific medical gas, whereby said adapters can be interchanged such that said apparatus can be used to test outlets or inlets for all specific medical gases.

23. The apparatus of claim 21 wherein said connector is specific to mate with the outlet or inlet for a specific medical gas, such that said apparatus can be used to test outlets or inlets only for said specific medical gases.

24. The apparatus of claim 21 further comprising a gas concentration transducer within said housing for producing an electrical signal related to the concentration of a specific gas oxygen within a medical gas sensed by said sensor, said electrical signal of gas concentration being transmitted to said computing device.

25. The apparatus of claim 24 further comprising a flow restrictor between said gas concentration transducer and said connector.

26. The apparatus of claim 24 wherein said gas concentration transducer comprises an oxygen transducer.

27. The apparatus of claim 21 wherein said flow sensing device comprises a bi-directional flow sensor for sensing the rate of flow of gas or vacuum through said connector.

28. The apparatus of claim 27 further comprising a flow transducer within said housing for producing an electrical signal related to the rate of flow of gas or vacuum through said connector sensed by said sensor, said electrical flow signal being transmitted to said computing device.

29. The apparatus of claim 21 further comprising a variable orifice between said connector and said flow sensing device for controlling the flow of gas between said connector and said flow sensing device.

30. The apparatus of claim 29 wherein said variable orifice comprises a manually operated ball valve.

31. The apparatus of claim 21 further comprising an exhaust outlet in said housing for venting gas from said medical gas system to outside of said housing.

32. The apparatus of claim 21 further comprising an analog-to-digital converter for converting electrical signals relating to said gas characteristics sensed by said sensing device to digital format and for transmitting said digital signals to said computing device.

33. The apparatus of claim 32 wherein said analog-to-digital converter comprises a PCMCIA card.

34. A method for testing and analysis of a medical gas system, comprising:

providing an apparatus having a computing device, a display device and a sensor for sensing data from said medical gas system, said display device and said sensor being coupled to said computing device, said sensor including a housing, at least one connector on said housing for mating said sensor with an outlet or inlet of said medical gas system, and a pressure or vacuum transducer and a flow sensing device within said housing;

mating said connector with an outlet or inlet of said medical gas system;

sensing data from said medical gas system by said sensor;

producing an electrical signal related to a gas pressure or vacuum sensed by said sensor, and transmitting said electrical gas pressure or vacuum signal to said computing device;

producing an electrical signal related to a gas flow rate sensed by said sensor, and transmitting said electrical gas flow rate signal to said computing device; and intepreting of said electrical signals by said computing device and generating a display on said display device related to the status or operation of said medical gas system.

35. The method of claim 34, wherein said sensor further comprises a gas concentration transducer within said housing, said method further comprising the steps of producing an electrical signal related to the concentration of a specific gas oxygen within a medical gas sensed by said sensor, and transmitting said electrical signal of gas concentration to said computing device.

36. The method of claim 34, wherein said apparatus further comprises interchangeable adapters attachable to said at least one connector and being specific to mate with the outlet or inlet for a specific medical gas, said method further comprising the steps of changing said adapters prior to mating said connector with an outlet or inlet of said medical gas system such that said apparatus can be used to test outlets or inlets for all specific medical gases.

37. The method of claim 34, wherein said apparatus further comprises an analog-to-digital converter, and said steps of transmitting electrical signals to said computing device comprise converting said electrical signals relating to said gas characteristics sensed by said sensing device into digital format and transmitting said digital signals to said computing device.

38. A method for testing compliance of a medical gas system with a preset standard, comprising:

providing an apparatus having a computing device, a display device and a sensor for sensing data from said medical gas system, said display device and said sensor being coupled to said computing device, said sensor including a housing, at least one connector on said housing for mating said sensor with an outlet or inlet of said medical gas system, and a pressure or vacuum transducer and a flow sensing device within said housing, and a variable orifice within said housing between said connector and said flow sensing device for controlling the flow of gas between said connector and said flow sensing device;

closing said variable orifice such that no gas can flow between said connector and said flow sensing device;

mating said connector with an outlet or inlet of said medical gas system;

sensing static gas pressure data from said medical gas system by said sensor;

producing an electrical signal related to a gas pressure or vacuum sensed by said sensor, and transmitting said electrical gas pressure or vacuum signal to said computing device;

manually opening said variable orifice;

continuing to sense gas pressure data from said medical gas system by said sensor;

when said measured gas pressure falls 5 psig, producing an electrical signal related to a gas flow rate sensed by said sensor, and transmitting said electrical gas flow rate signal to said computing device;

interpreting of said electrical signals by said computing device; and comparing said gas flow rate data with a preset gas flow rate standard and generating a display on said display device related to the flow rate measurement for said gas as a function of the compliance of said medical gas system with a preset standard.

* * * * *